(12) United States Patent
Yasunaga

(10) Patent No.: US 9,510,890 B2
(45) Date of Patent: Dec. 6, 2016

(54) TREATMENT DEVICE FOR MEDICAL TREATMENT

(71) Applicant: OLYMPUS CORPORATION, Tokyo (JP)

(72) Inventor: Shinji Yasunaga, Higashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 286 days.

(21) Appl. No.: 14/162,876

(22) Filed: Jan. 24, 2014

(65) Prior Publication Data

US 2014/0142562 A1 May 22, 2014

Related U.S. Application Data

(63) Continuation of application No. PCT/JP2012/068610, filed on Jul. 23, 2012.

(30) Foreign Application Priority Data

Jul. 25, 2011 (JP) ................................. 2011-161898

(51) Int. Cl.
*A61B 18/10* (2006.01)
*A61B 18/08* (2006.01)
(Continued)

(52) U.S. Cl.
CPC ............ *A61B 18/08* (2013.01); *A61B 18/085* (2013.01); *A61B 18/1445* (2013.01); *A61B 18/10* (2013.01);
(Continued)

(58) Field of Classification Search
CPC ........... A61B 2018/00714; A61B 2018/00791;
A61B 2018/00815; A61B 2018/00821;
A61B 18/08; A61B 18/082; A61B 18/10
See application file for complete search history.

(56) References Cited

U.S. PATENT DOCUMENTS 5,553,622 A    9/1996  McKown et al.
5,720,293 A *  2/1998  Quinn .................... A61B 5/028
                                                            600/505

(Continued)

FOREIGN PATENT DOCUMENTS

JP    H06-511172 A    12/1994
JP    H07-504097 A     5/1995
(Continued)

OTHER PUBLICATIONS

Japanese Office Action dated Apr. 21, 2015 from related Japanese Patent Application No. 2011-161898, together with an English language translation.

(Continued)

*Primary Examiner* — Jaymi Della
(74) *Attorney, Agent, or Firm* — Scully, Scott, Murphy & Presser, P.C.

(57) ABSTRACT

A treatment device for a medical treatment heats a biotissue at a desired temperature, and includes a treatment tool, a controller and a storage section. The treatment tool includes a heat transfer portion which contacts with the biotissue to transfer heat to the biotissue, and a resistance element into which power is supplied to heat the heat transfer portion. The controller is detachably attached to the treatment tool, and measures a resistance value R of the resistance element. The storage section stores a coefficient C2. The controller calculates a coefficient C1 based on a calibration temperature when the treatment tool is connected to the controller. The controller calculates a temperature of the resistance
(Continued)

element using the R, C1 and C2, and controls the temperature of the heat transfer portion.

6 Claims, 11 Drawing Sheets

(51) Int. Cl.
    *A61B 18/14*     (2006.01)
    *A61B 18/00*     (2006.01)

(52) U.S. Cl.
    CPC ............... *A61B 2018/00595* (2013.01); *A61B 2018/00714* (2013.01); *A61B 2018/00791* (2013.01); *A61B 2018/00815* (2013.01)

(56) References Cited

U.S. PATENT DOCUMENTS

| | | | |
|---|---|---|---|
| 5,807,269 | A | 9/1998 | Quinn et al. |
| 6,423,056 | B1 | 7/2002 | Ishikawa et al. |
| 2005/0222560 | A1 | 10/2005 | Kimura et al. |
| 2008/0097559 | A1 | 4/2008 | Eggers et al. |
| 2010/0204694 | A1 | 8/2010 | Mehta et al. |
| 2012/0022517 | A1* | 1/2012 | Stuebe ............... A61B 18/085 606/31 |

FOREIGN PATENT DOCUMENTS

| | | | |
|---|---|---|---|
| JP | 2000-339039 A | 12/2000 | |
| JP | 2001-190561 A | 7/2001 | |
| JP | 2007-037845 A | 2/2007 | |
| JP | 2010-065661 A | 3/2010 | |
| WO | WO 9315654 A1 * | 8/1993 | ............ A61B 5/028 |

OTHER PUBLICATIONS

Extended Supplementary European Search Report dated Dec. 5, 2014 from related European Application No. 12 81 7898.5.

International Search Report dated Aug. 14, 2012 issued in PCT/JP2012/068610.

European Patent Communication dated Mar. 16, 2016 from corresponding European Application No. 12 817 898.5.

\* cited by examiner

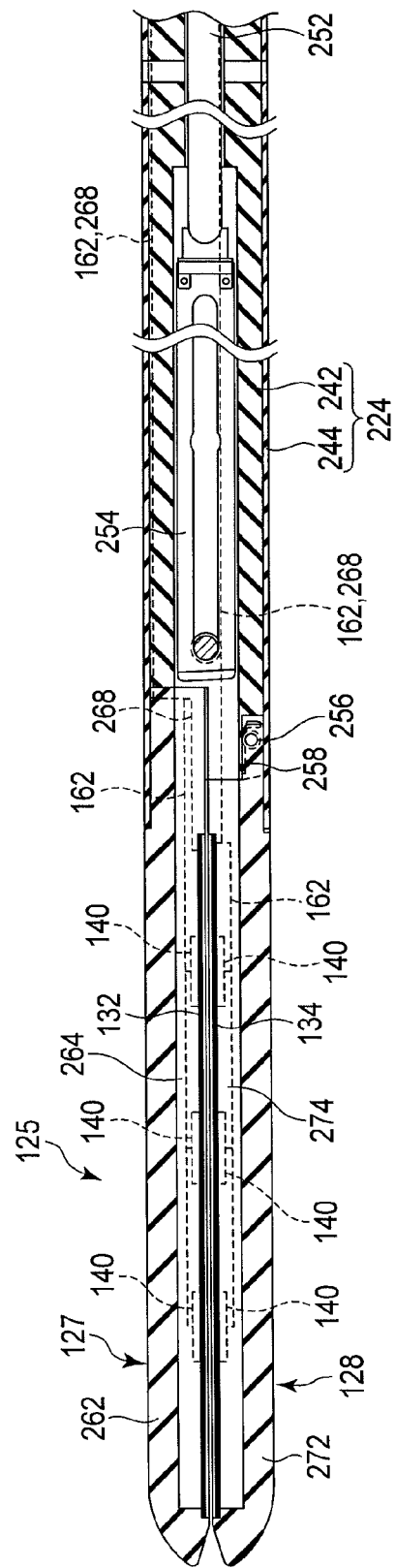
F I G. 2A

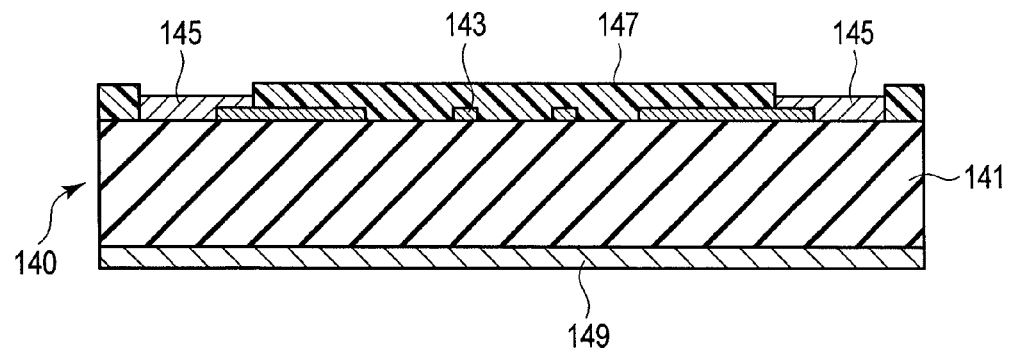
F I G. 4B
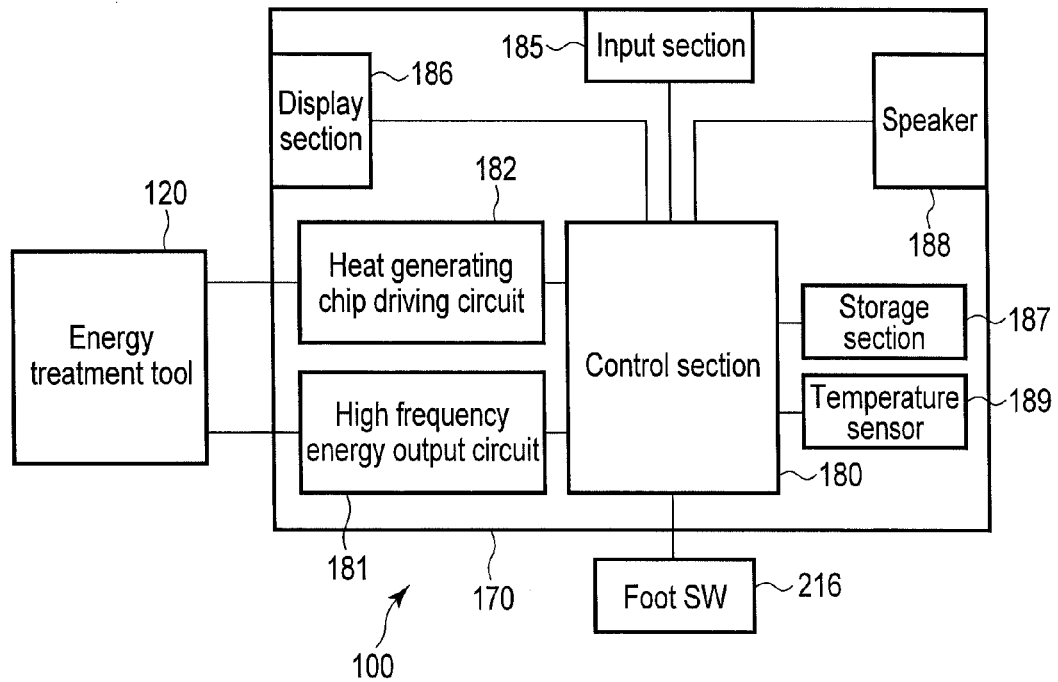
F I G. 5

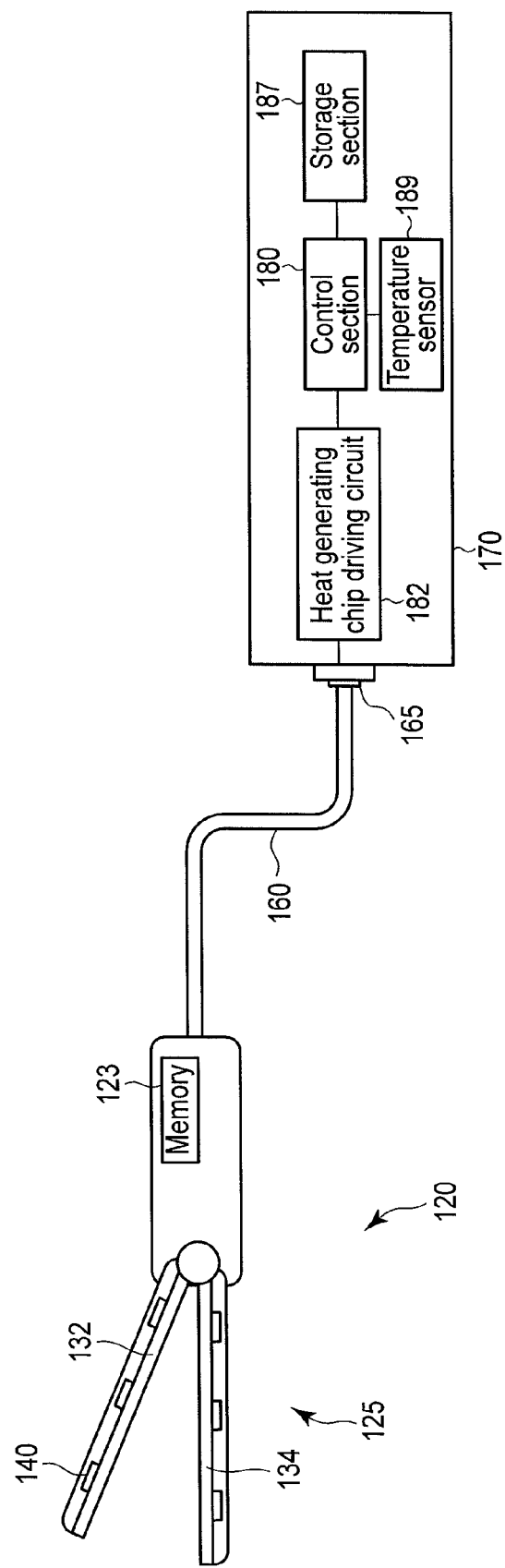
F I G. 6

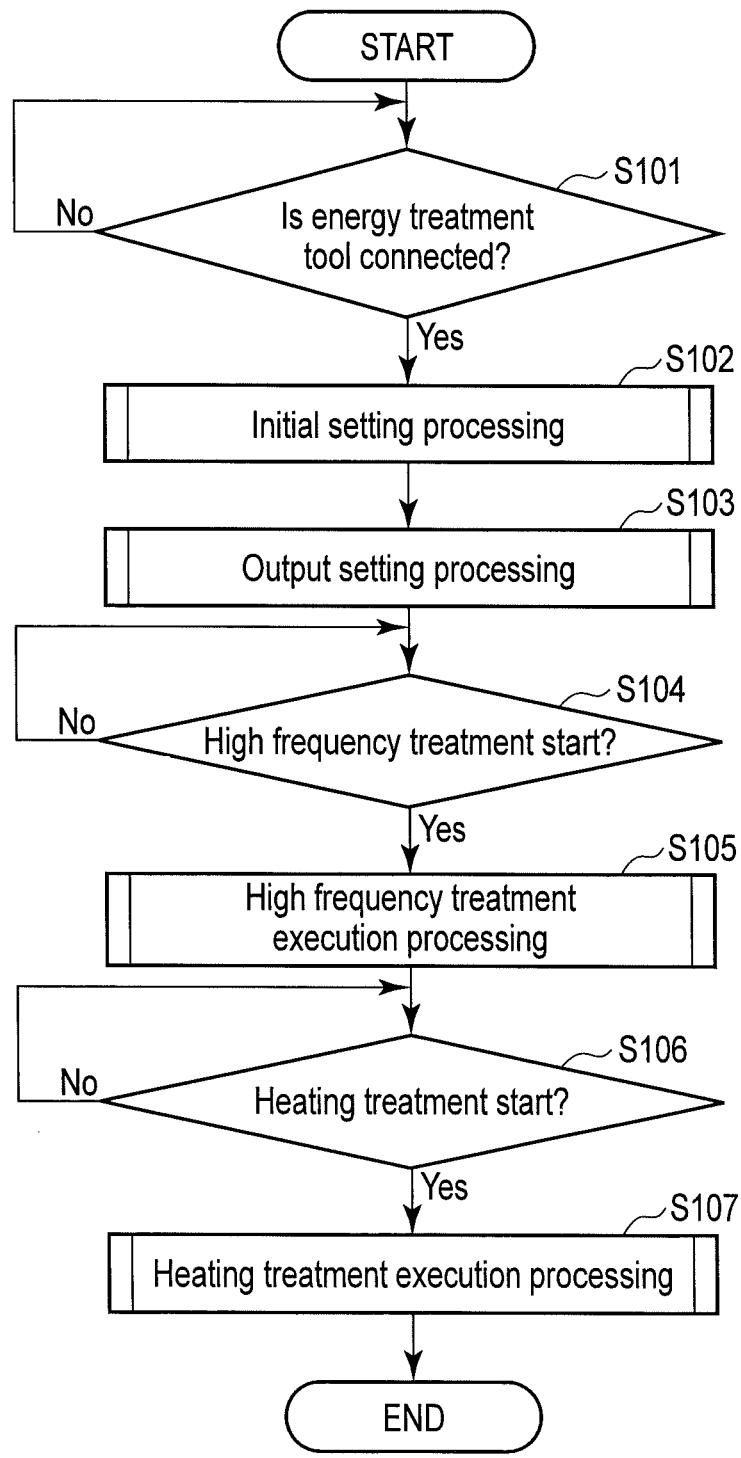
F I G. 7

TREATMENT DEVICE FOR MEDICAL TREATMENT

CROSS-REFERENCE TO RELATED APPLICATIONS

This application is a Continuation application of PCT Application No. PCT/JP2012/068610, filed Jul. 23, 2012 and based upon and claiming the benefit of priority from prior Japanese Patent Application No. 2011-161898, filed Jul. 25, 2011, the entire contents of all of which are incorporated herein by reference.

BACKGROUND OF THE INVENTION

1. Field of the Invention

The present invention relates to a treatment device for a medical treatment.

2. Description of the Related Art

In general, a treatment device for a medical treatment is known which treats a biotissue by use of heat energy. For example, in Jpn. Pat. Appln. KOKAI Publication No. 2001-190561, the following treatment device for the medical treatment is disclosed. This treatment device for the medical treatment has an openable/closable holding portion to hold a biotissue that is a treatment object. In this holding portion, a resistance element is disposed which functions as a heater to heat the holding portion. In such a treatment device for the medical treatment, the biotissue is held by the holding portion, and the biotissue of the held portion is heated, whereby the biotissue can be anastomosed. As to control of an amount of power to be introduced into the resistance element, in Jpn. Pat. Appln. KOKAI Publication No. 2001-190561, there are disclosed a control method of introducing the power of the amount of a predetermined constant value, and a method of controlling a temperature of the resistance element to a predetermined temperature by feedback control while performing temperature measurement on the basis of a change of a resistance value of the resistance element.

In use of such a treatment device for a medical treatment as described above, it is general that an area of a biotissue to be held by a holding portion during anastomosis is not constant and varies in every treatment. Consequently, in a control method in which an amount of power to be introduced into a resistance element that functions as a heater is set to a predetermined constant value, an anastomosis temperature varies in every treatment. As a result, there is the possibility that a joining strength becomes unstable. On the other hand, in a method in which the temperature of the resistance element is controlled to a predetermined temperature by feedback control while performing temperature measurement on the basis of a change of a resistance value of the resistance element, it is necessary to accurately acquire characteristics of a relation between the resistance value and the temperature of the resistance element in advance. For this purpose, it is necessary to manage uniformity of the resistance element with high precision during manufacturing, or to accurately measure the resistance-temperature characteristics of the resistance element individually. As a result, costs of the device increase disadvantageously.

BRIEF SUMMARY OF THE INVENTION

An object of the present invention is to provide a treatment device for a medical treatment in which, at low cost and without the need for individually acquiring a relation between a resistance value and a temperature of a resistance element in advance, the temperature of the resistance element can be calculated from the resistance value thereof, to execute accurate temperature control.

To achieve the above described object, according to an aspect of the invention, a treatment device for a medical treatment which heats a biotissue at a desired temperature to perform the medical treatment includes a treatment tool which includes a heat transfer portion which comes in contact with the biotissue to transfer heat to the biotissue, and a resistance element into which power is supplied to heat the heat transfer portion; a controller which is detachably attached to the treatment tool, and configured to measure a resistance value R of the resistance element, and supplies the power to the resistance element so as to control a temperature of the heat transfer portion to heat the biotissue at the desired temperature; and a storage section which is disposed in the treatment tool or the controller to store a coefficient C2, wherein the controller is configured to calculate a coefficient C1 based on a calibration temperature in a state where the treatment tool is connected to the controller, calculate a temperature T of the resistance element, using the coefficient C1, the resistance value R and the coefficient C2, in accordance with $T = C1 \times R + C2$, and control the temperature of the heat transfer portion by use of the temperature T.

According to the present invention, there can be provided a treatment device for a medical treatment in which, at low cost and without the need for individually acquiring a relation between a resistance value and a temperature of a resistance element in advance, the temperature of the resistance element can be calculated from the resistance value thereof, to execute accurate temperature control since a coefficient C2 is stored in advance and a coefficient C1 is calculated in a state where a treatment tool is connected to a controller.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is a schematic view of a cross section showing a configuration example of a shaft and a holding portion of an energy treatment tool according to the one embodiment of the present invention, and shows a state where the holding portion is closed;

FIG. 4B is a view schematically showing the configuration example of the heat generating chip according to the one embodiment of the present invention, and is a sectional view taken along the 4B-4B line shown in FIG. 4A;

FIG. 5 is a view showing a configuration example of a controller according to the one embodiment of the present invention;

FIG. 6 is a view schematically showing one example of a configuration concerning a heating treatment of a treatment device for a medical treatment according to the one embodiment of the present invention;

FIG. 7 is a flowchart showing one example of processing by a control section of the treatment device for the medical treatment according to the one embodiment of the present invention;

DETAILED DESCRIPTION OF THE INVENTION

Figure 1:
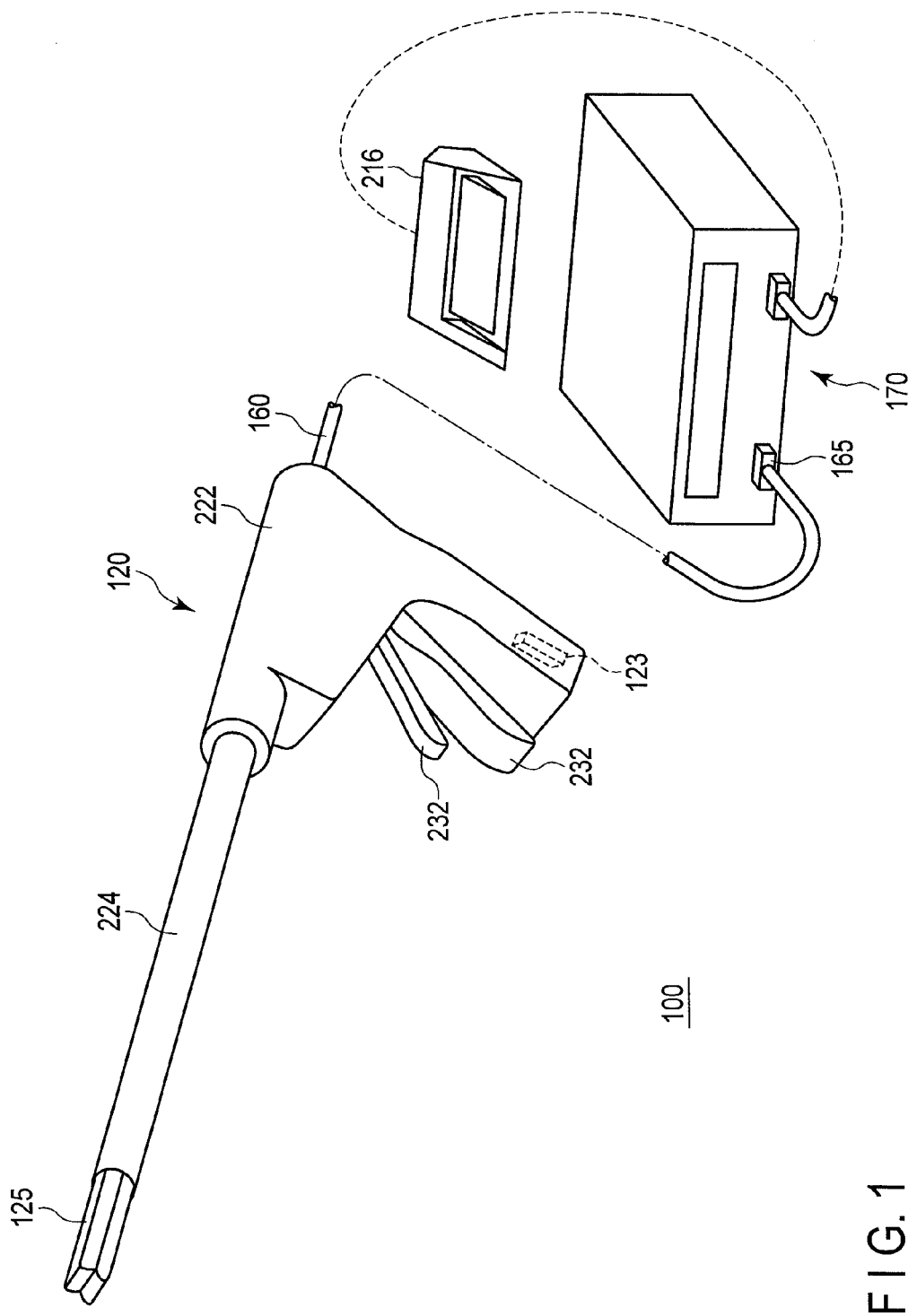
FIG. 1 is a schematic view showing a configuration example of a treatment system for a medical treatment according to one embodiment of the present invention.

One embodiment of the present invention will be described with reference to the drawings. A treatment device for a medical treatment according to the present embodiment is a device for use in the medical treatment of a biotissue, and a device which applies high frequency energy and heat energy to the biotissue. As shown in FIG. 1, a treatment device 100 for the medical treatment includes an energy treatment tool 120, a controller 170, and a foot switch 216.

The energy treatment tool 120 is a linear type treatment tool for a surgical treatment, for example, for passing through an abdominal wall to perform the treatment. The energy treatment tool 120 has a handle 222, a shaft 224 attached to the handle 222, and a holding portion 125 disposed at the tip of the shaft 224. The holding portion 125 is an openable and closable treatment portion which holds a biotissue of a treatment object, to perform a treatment such as coagulation or incision of the biotissue. Hereinafter, for explanation, a holding portion 125 side will be referred to as a distal side, and a handle 222 side will be referred to as a proximal side. The handle 222 includes operation knobs 232 to operate the holding portion 125. Moreover, a portion of the handle 222 includes a non-volatile memory 123. In the memory 123, as described later in detail, there are stored an identification number inherent in the energy treatment tool 120, and inherent information such as an inherent coefficient C2 for use in temperature control. It is to be noted that a shape of the energy treatment tool 120 shown herein is, needless to say, one example, and may be any shape as long as the tool has a similar function. For example, the tool may have such a shape as forceps, or the shaft may be bent.

The handle 222 is connected to the controller 170 via a cable 160. Here, the cable 160 is connected to the controller 170 by a connector 165, and this connection is detachably attached. That is, in the treatment device 100 for the medical treatment, the energy treatment tool 120 can be changed for every treatment. The controller 170 is connected to the foot switch 216. The foot switch 216 to be operated by a foot may be replaced with a switch to be operated by a hand or another switch. An operator operates a pedal of the foot switch 216, to switch ON/OFF of supply of energy from the controller 170 to the energy treatment tool 120.

Figure 2B:
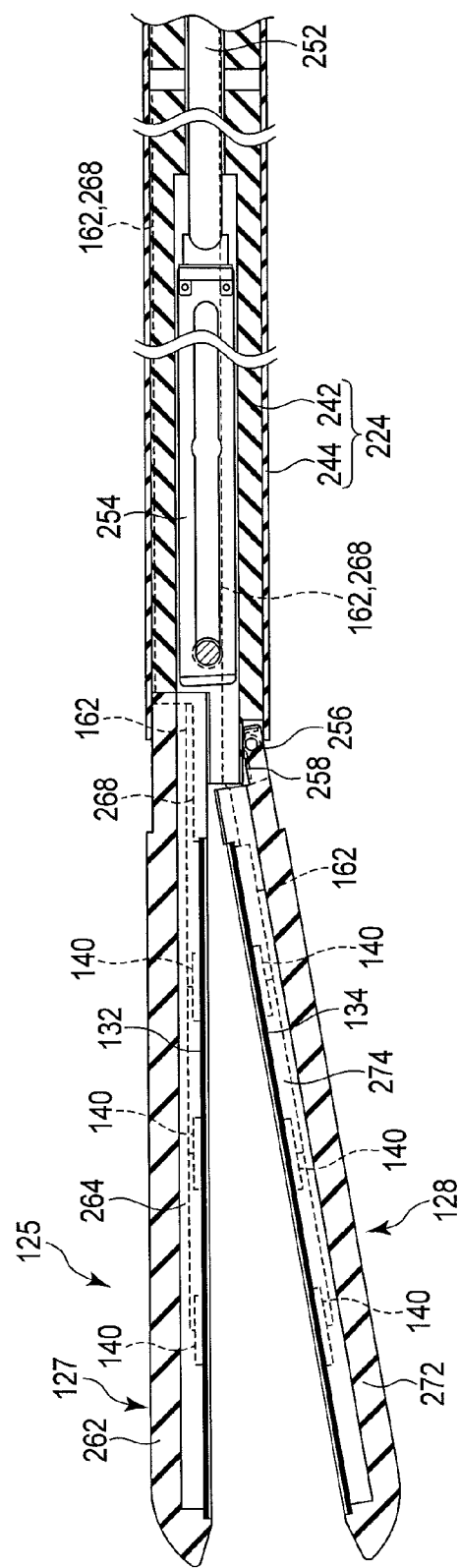
FIG. 2B is a schematic view of a cross section showing the configuration example of the shaft and the holding portion of the energy treatment tool according to the one embodiment of the present invention, and shows a state where the holding portion is opened.

One example of a structure of the holding portion 125 and the shaft 224 is shown in FIGS. 2A and 2B. FIG. 2A shows a state where the holding portion 125 is closed, and FIG. 2B shows a state where the holding portion 125 is opened. The shaft 224 includes a tubular body 242 and a sheath 244. The tubular body 242 is fixed to the handle 222 by a proximal portion of the tubular body. The sheath 244 is disposed on an outer periphery of the tubular body 242 so that the sheath is slidable along an axial direction of the tubular body 242.

In a distal portion of the tubular body 242, the holding portion 125 is disposed. The holding portion 125 includes a first holding member 127 and a second holding member 128. A proximal portion of the first holding member 127 is fixed to the distal portion of the tubular body 242 of the shaft 224. On the other hand, a proximal portion of the second holding member 128 is rotatably supported in the distal portion of the tubular body 242 of the shaft 224 by a support pin 256. Therefore, the second holding member 128 rotates around an axis of the support pin 256, and opens from the first holding member 127 and closes thereto.

In the state where the holding portion 125 is closed, a cross sectional shape of the proximal portion of the first holding member 127 which is combined with the proximal portion of the second holding member 128 is a round shape. The second holding member 128 is urged by an elastic member 258 such as a leaf spring so that the second holding member opens from the first holding member 127. When the sheath 244 is slid along the tubular body 242 to the distal side to cover, with the sheath 244, the proximal portion of the first holding member 127 and the proximal portion of the second holding member 128, the first holding member 127 and the second holding member 128 close against an urging force of the elastic member 258, as shown in FIG. 2A. On the other hand, when the sheath 244 is slid to the proximal side of the tubular body 242, the second holding member 128 opens from the first holding member 127 by the urging force of the elastic member 258, as shown in FIG. 2B.

Into the tubular body 242, as described later, there are inserted energization lines 268 for a high frequency electrode which are to be connected to a first high frequency electrode 132 or a second high frequency electrode 134, and energization lines 162 for heat generating chips which are to be connected to heat generating chips 140 that are heat generation members. In the tubular body 242, a driving rod 252 connected to one of the operation knobs 232 on the proximal side thereof is movably disposed along the axial direction of the tubular body 242. On the distal side of the driving rod 252, a thin plate-like cutter 254 provided with a blade on the distal side is disposed. When the operation knob 232 is operated, the cutter 254 is moved along the axial direction of the tubular body 242 via the driving rod 252. When the cutter 254 moves to the distal side, the cutter 254 is contained in cutter guide grooves 264 and 274 formed in the holding portion 125 as described later.

Figure 3A:
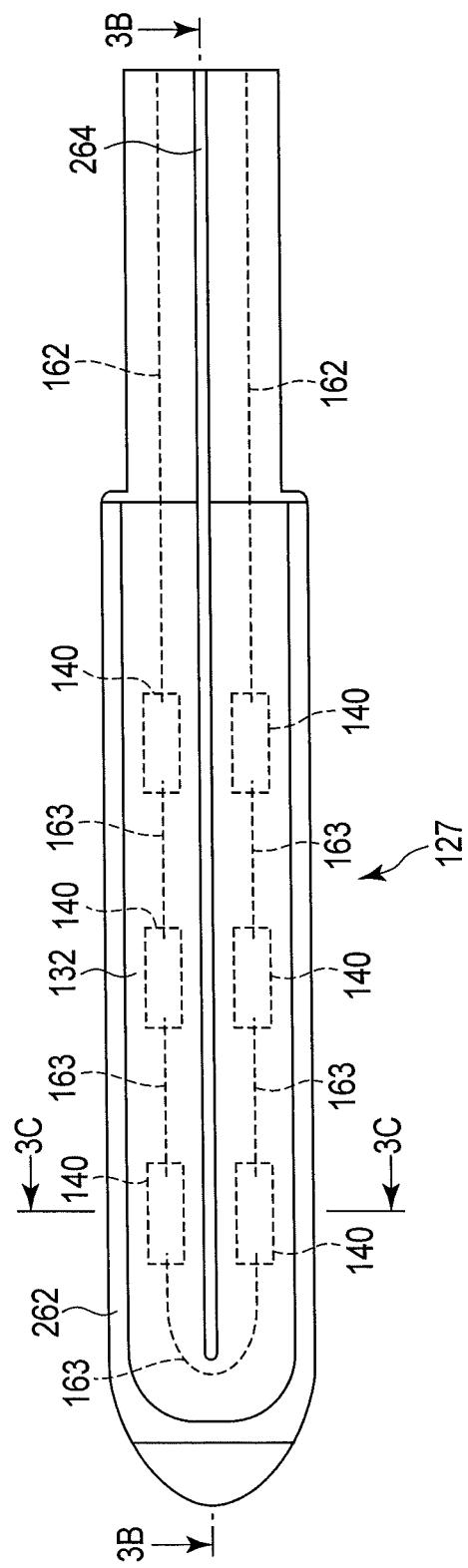
FIG. 3A is a plan view schematically showing a configuration example of a first holding member of the holding portion according to the one embodiment of the present invention.
Figure 3B:
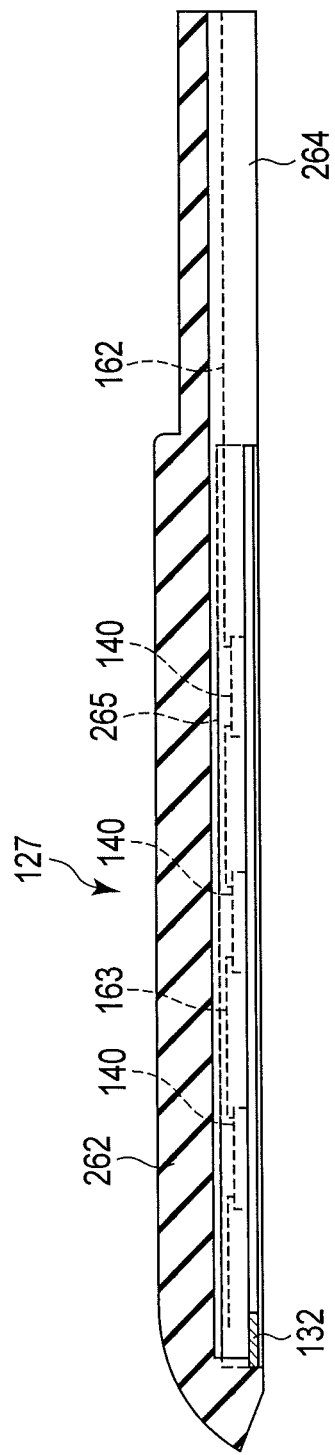
FIG. 3B is a view schematically showing the configuration example of the first holding member of the holding portion according to the one embodiment of the present invention, and is a longitudinal sectional view taken along the 3B-3B line of FIG. 3A.
Figure 3C:
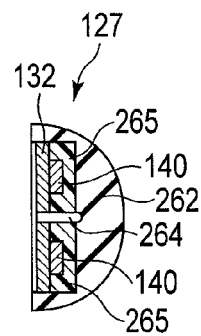
FIG. 3C is a view schematically showing the configuration example of the first holding member of the holding portion according to the one embodiment of the present invention, and is a cross-sectional view taken along the 3C-3C line of FIG. 3A.

The first holding member 127 has a first holding member main body 262, and the second holding member 128 has a second holding member main body 272. As shown in FIGS. 3A, 3B and 3C, in the first holding member main body 262, the cutter guide groove 264 is formed to guide the cutter 254 described above. In the first holding member main body 262, a concave portion is disposed, in which the first high frequency electrode 132 made of, for example, a copper thin plate is disposed. The first high frequency electrode 132 has the cutter guide groove 264, and hence a planar shape of the electrode is substantially a U-shape as shown in FIG. 3A.

Moreover, as described later in detail, the heat generating chips 140 are joined to the surface of the first high frequency electrode 132 on the side of the first holding member main body 262. To cover the heat generating chips 140, wiring lines and the like to the heat generating chips 140 and the first high frequency electrode 132, a sealant made of, for example, silicone is applied to form a sealing film 265. The first high frequency electrode 132 is electrically connected to the energization line 268 for the high frequency electrode as shown in FIGS. 2A and 2B. The first high frequency electrode 132 is connected to the cable 160 via the energization line 268 for this high frequency electrode.

The second holding member 128 has a shape symmetrical to the first holding member 127. That is, at a position of the second holding member 128 which faces the cutter guide groove 264, the cutter guide groove 274 is formed. Moreover, at a position of the second holding member main body 272 which faces the first high frequency electrode 132, the second high frequency electrode 134 is disposed. The second high frequency electrode 134 is connected to the cable 160 via the energization line 268 for the high frequency electrode.

When the closed holding portion 125 holds the biotissue, the held biotissue comes in contact with the first high frequency electrode 132 and the second high frequency electrode 134. The first holding member 127 and the second holding member 128 further have mechanisms for heat generation, to cauterize the biotissue which comes in contact with the first high frequency electrode 132 and the second high frequency electrode 134. The heat generation mechanism disposed in the first holding member 127 has a configuration similar to the heat generation mechanism disposed in the second holding member 128. Here, the heat generation mechanism formed in the first holding member 127 will be described as an example.

Figure 4A:
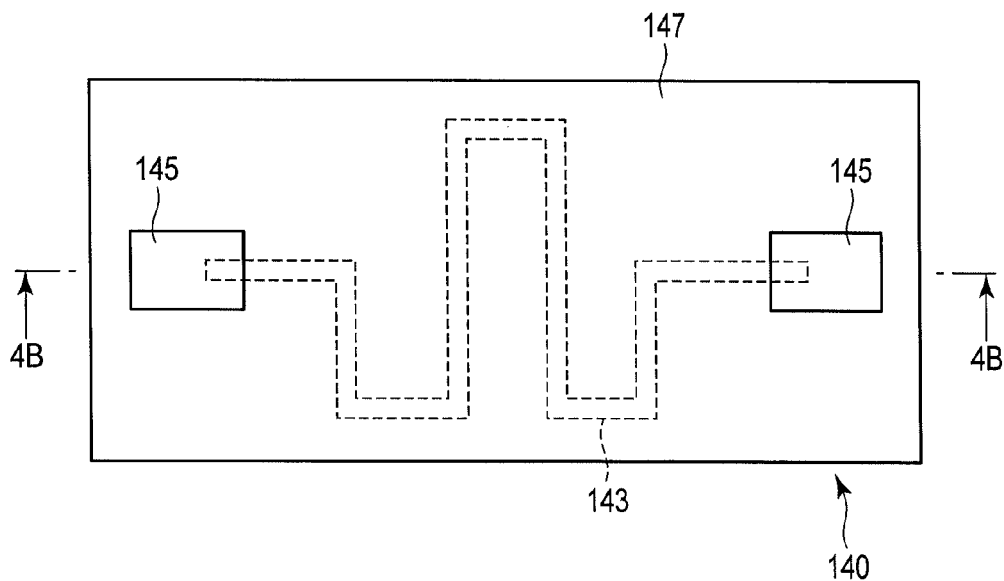
FIG. 4A is a top view schematically showing a configuration example of a heat generating chip according to the one embodiment of the present invention.

First, the heat generating chips 140 including this heat generation mechanism will be described with reference to FIG. 4A and FIG. 4B. Here, FIG. 4A is a top view, and FIG. 4B is a sectional view taken along the 4B-4B line shown in FIG. 4A. Each of the heat generating chips 140 is formed by using a substrate 141 made of alumina. On a front surface which is one of main surfaces of the substrate 141, a resistance pattern 143 is formed which is a Pt thin film for the heat generation. Moreover, in the vicinities of two short sides of a rectangular shape of the front surface of the substrate 141, rectangular electrodes 145 are formed, respectively. Here, the electrodes 145 are connected to ends of the resistance pattern 143, respectively. On the front surface of the substrate 141 excluding portions in which the electrodes 145 are formed and including a portion on the resistance pattern 143, an insulation film 147 made of, for example, polyimide is formed.

On the whole back surface of the substrate 141, a joining metal layer 149 is formed. The electrodes 145 and the joining metal layer 149 are multilayer films made of, for example, Ti, Cu, Ni, and Au. The electrodes 145 and the joining metal layer 149 have a stable strength against soldering or the like. The joining metal layer 149 is disposed to stabilize the joining, for example, when the heat generating chips 140 are soldered to the first high frequency electrode 132.

The heat generating chips 140 are disposed on the surfaces (second main surfaces) of the first high frequency electrode 132 and the second high frequency electrode 134 on a side opposite to the surfaces (first main surfaces) thereof which come in contact with the biotissue. Here, each of the heat generating chips 140 is fixed, respectively, by soldering the front surface of the joining metal layer 149 to the second main surface of the first high frequency electrode 132 or the second high frequency electrode 134.

The first high frequency electrode 132 will be described as an example with reference to FIGS. 3A, 3B and 3C. In the first high frequency electrode 132, the six heat generating chips 140 are disposed in a discrete manner. That is, three of the heat generating chips 140 are arranged in each of two rows symmetrically via the cutter guide groove 264 from the proximal side toward the distal side.

The resistance patterns 143 of these heat generating chips 140 are connected in series via the electrodes 145. The adjacent electrodes 145 are connected to each other by a wire 163 formed, for example, by wire bonding. Both ends of the heat generating chips connected in series are connected to a pair of energization lines 162 for the heat generating chips. The pair of energization lines 162 for the heat generating chips are connected to the cable 160. In this way, the heat generating chips 140 are connected to the controller 170 via the wires 163, the energization lines 162 for the heat generating chips and the cable 160. The controller 170 controls the power to be introduced into the heat generating chips 140.

As above, in the present embodiment, a plurality of the heat generating chips 140 are disposed on the first high frequency electrode 132, but the chips are disposed to enhance temperature uniformity of the first high frequency electrode 132, and all the six heat generating chips 140 can electrically be regarded as a single heat generating chip. The sealant made of, for example, silicone is applied onto the first high frequency electrode 132 to cover the heat generating chips 140 and the energization lines 162 for the heat generating chips, whereby the sealing film 265 is formed as shown in FIGS. 3A, 3B and 3C.

A current output from the controller 170 flows through the respective resistance patterns 143 of the six heat generating chips 140. As a result, the respective resistance patterns 143 generate heat. When the resistance patterns 143 generate the heat, the heat is transferred to the first high frequency electrode 132. By this heat, the biotissue which comes in contact with the first high frequency electrode 132 is cauterized.

For efficiently transferring the heat generated in the heat generating chips 140 to the first high frequency electrode 132, the sealing film 265 and the first holding member main body 262 around the film preferably have a thermal conductivity lower than a thermal conductivity of the first high frequency electrode 132 or the substrate 141. With the result that the thermal conductivities of the sealing film 265 and the first holding member main body 262 are low, heat conduction having less loss is realized.

In the controller 170, as shown in FIG. 5, there are disposed a control section 180, a high frequency energy output circuit 181, a heat generating chip driving circuit 182, an input section 185, a display section 186, a storage section 187, a speaker 188, and a temperature sensor 189. The control section 180 is connected to each section in the controller 170, to control each section of the controller 170. The high frequency energy output circuit 181 is connected to the energy treatment tool 120, and drives the first high frequency electrode 132 and the second high frequency electrode 134 of the energy treatment tool 120 under the control of the control section 180. That is, the high frequency energy output circuit 181 applies high frequency voltages to the first high frequency electrode 132 and the second high frequency electrode 134 via the energization lines 268 for the high frequency electrodes.

The heat generating chip driving circuit 182 is connected to the energy treatment tool 120, and drives the heat generating chips 140 of the energy treatment tool 120 under the control of the control section 180. That is, the heat generating chip driving circuit 182 supplies the power to the resistance patterns 143 of the heat generating chips 140 via the energization lines 162 for the purpose of heating under the control of the control section 180. Here, the heat generating chip driving circuit 182 can change an amount of the power to be supplied to the heat generating chips 140. Moreover, the heat generating chip driving circuit 182 has a function of measuring the current which flows when the voltage is applied to the heat generating chips 140. The heat generating chip driving circuit 182 outputs a measured current value to the control section 180.

A resistance value of the resistance patterns 143 changes in accordance with a temperature of the resistance patterns 143. Therefore, when the control section 180 has a relation between the temperature and the resistance value of the resistance patterns 143, the control section can acquire the temperature of the resistance patterns 143 on the basis of the resistance value of the resistance patterns 143. The control section 180 calculates the resistance value of the resistance patterns 143 on the basis of a value of the voltage applied to the resistance patterns 143, and a value of the current flowing at this time which is acquired from the heat generating chip driving circuit 182. Furthermore, the control section 180 calculates the temperature of the resistance patterns 143 on the basis of the relation between the temperature and the resistance value of the resistance patterns 143.

Moreover, the control section 180 calculates the relation between the temperature and the resistance value of the resistance patterns 143, to acquire the temperature of the resistance patterns 143 as described above. More specifically, the control section 180 reads inherent information of the energy treatment tool 120 from the memory 123, when the energy treatment tool 120 is connected to the controller 170 via the connector 165. Furthermore, a low voltage is applied to the resistance patterns 143 of the heat generating chips 140 under the control of the control section 180, and the control section 180 acquires the resistance value of the resistance patterns 143 on the basis of the value of the current flowing at this time. Additionally, the control section 180 acquires an environmental temperature as a calibration temperature from the temperature sensor 189. The control section 180 calculates the relation between the temperature and the resistance value of the resistance patterns 143 from characteristics of the energy treatment tool 120, the resistance value of the resistance patterns 143 and the environmental temperature. Moreover, as described later in detail, the control section 180 stores, in the storage section 187, an identification number of the energy treatment tool 120 in the inherent information read from the memory 123, and a value concerning the relation between the calculated temperature and the resistance value, i.e., a coefficient C1 described later in detail.

The control section 180 is connected to the foot switch (SW) 216, and ON indicating that a treatment by the energy treatment tool 120 is to be performed and OFF indicating that the treatment is to be stopped are input from the foot switch 216. The input section 185 is input various settings and the like of the control section 180. The display section 186 displays various information of the treatment device 100 for the medical treatment under the control of the control section 180. In the storage section 187, various pieces of data required for an operation of the controller 170 are stored. The speaker 188 outputs an alarm sound or the like. The temperature sensor 189 measures the environmental temperature.

A schematic view in which a portion concerning a heating treatment is especially extracted from the treatment device 100 for the medical treatment described above is shown in FIG. 6. As shown in this drawing, the heating treatment is performed by the energy treatment tool 120 including the holding portion 125 having the first high frequency electrode 132 and the second high frequency electrode 134 and the heat generating chips 140, and the memory 123. The control of the energy treatment tool 120 is executed by the controller 170 having the control section 180, the heat generating chip driving circuit 182, the storage section 187 and the temperature sensor 189. The energy treatment tool 120 is connected to the controller 170 by the detachably attached cable 160 by use of the connector 165 disposed on the side of the controller 170. It is to be noted that the above-mentioned configuration concerning the high frequency treatment or the cutter is not necessarily required in the treatment device 100 for the medical treatment according to the present invention.

In this way, for example, the first high frequency electrode 132 or the second high frequency electrode 134 functions as a heat transfer portion which comes in contact with the biotissue to transfer the heat to the biotissue. For example, the heat generating chips 140 function as resistance elements into which the power is introduced to heat the heat transfer portions. For example, the energy treatment tool 120 functions as a treatment tool having the heat transfer portions and the resistance elements. For example, the controller 170 functions as a controller which can measure a resistance value R of the resistance elements and supply the power to the resistance elements to control the temperature of the heat transfer portions, for the purpose of heating the biotissue at a desired temperature. For example, the memory 123 functions as a storage section for storing a coefficient C2. For example, the temperature sensor 189 functions as a temperature sensor for measuring the environmental temperature. For example, the storage section 187 functions as a calculated coefficient storage section.

Next, an operation of the treatment device 100 for the medical treatment according to the present embodiment will be described. A flowchart of processing by the control section 180 is shown in FIG. 7. In step S101, the control section 180 determines whether or not the cable 160 connected to the energy treatment tool 120 is connected to the controller 170 via the connector. When the cable is not connected, the control section 180 repeats the step S101. On the other hand, when the control section 180 determines that the cable 160 connected to the energy treatment tool 120 is connected to the controller 170, the processing goes to step S102. In the step S102, the control section 180 executes initial setting processing which is defined processing. This initial setting processing will be described later in detail.

In step S103, the control section 180 executes output setting processing which is defined processing. In the output setting processing, the control section 180 receives an operator's instruction via the input section 185, and sets output conditions of the treatment device 100 for the medical treatment, for example, a set power of a high frequency energy output, a desired temperature $T_{op}$ by a heat energy output, a heating time $t_{op}$, and the like. Here, the operator may individually set each value, or the operator may select a set of the set values in accordance with an operation type, and the control section 180 may determine the output conditions on the basis of the selection.

The holding portion 125 and the shaft 224 of the energy treatment tool 120 are inserted, for example, into an abdominal cavity through the abdominal wall. The operator operates the operation knobs 232 to open and close the holding portion 125, so that the biotissue of the treatment object is held by the first holding member 127 and the second holding member 128. At this time, the biotissue of the treatment object comes in contact with the first main surfaces of both the first high frequency electrode 132 disposed in the first holding member 127 and the second high frequency electrode 134 disposed in the second holding member 128.

In step S104, the control section 180 repeats determination of whether or not the instruction of high frequency treatment start by the operator has been input. The operator operates the foot switch 216, when the biotissue of the treatment object is held by the holding portion 125. For example, the foot switch 216 is switched ON, and the control section 180 determines that the instruction of the high frequency treatment start is input. At this time, in step S105, the control section 180 executes high frequency treatment execution processing. In the high frequency treatment execution processing, a high frequency power of the set power is supplied from the high frequency energy output circuit 181 of the controller 170 to the first high frequency electrode 132 and the second high frequency electrode 134 via the cable 160. The power to be supplied is, for example, from about 20 W to 80 W. As a result, the biotissue generates the heat, and the tissue is cauterized. By this cauterization, the tissue is denatured, and coagulated. After elapse of a predetermined time, or on the basis of the operator's instruction, the control section 180 stops the output of the high frequency energy, and the high frequency treatment execution processing ends.

In step S106, the control section 180 repeats determination of whether or not the instruction of heating treatment start by the operator has been input. For example, when the foot switch 216 is switched ON and the control section 180 determines that the instruction of the heating treatment start is input, the control section 180 executes heating treatment execution processing in step S107. In the heating treatment execution processing, the controller 170 supplies the power to the heat generating chips 140 so that the temperature of the first high frequency electrode 132 reaches the desired temperature, as described later in detail. Here, the desired temperature is, for example, about 200° C. At this time, the current flows through the resistance patterns 143 of the respective heat generating chips 140 from the heat generating chip driving circuit 182 of the controller 170 via the cable 160 and the energization lines 162 for the heat generating chips. The resistance patterns 143 of the respective heat generating chips 140 generate the heat by the current.

The heat generated in the resistance patterns 143 is transferred to the first high frequency electrode 132 via the substrate 141 and the joining metal layer 149. As a result, the temperature of the first high frequency electrode 132 rises. Similarly, the temperature of the second high frequency electrode 134 also rises due to the heat generation by the current flowing through the respective heat generating chips 140 disposed in the second high frequency electrode 134. By this heat, the biotissue which comes in contact with the first main surface of the first high frequency electrode 132 or the second high frequency electrode 134 is further cauterized, and further coagulated. When the biotissue is coagulated by the heating, the output of the heat energy is stopped, and the heating treatment execution processing ends. As described above, a series of processes by the control section 180 ends. Finally, the operator operates the operation knobs 232 to move the cutter 254, and cuts the biotissue. As described above, the treatment of the biotissue is completed.

In such a heating treatment as described above, high precision is required for the temperature control in the heating by the heat generating chips 140. In the present embodiment, the control section 180 acquires the temperature of the heat generating chips 140 on the basis of the resistance value of the resistance patterns 143. That is, under the control of the control section 180, the heat generating chip driving circuit 182 applies the voltage to the resistance patterns 143, and measures a value of the current flowing at this time. The heat generating chip driving circuit 182 outputs the measured current value to the control section 180. The control section 180 calculates the resistance value of the resistance patterns 143 on the basis of the value of the voltage applied to the resistance patterns 143 and the current value acquired from the heat generating chip driving circuit 182. The control section 180 calculates the temperature of the resistance patterns 143 on the basis of the calculated resistance value and a relation between the resistance value and the temperature of the resistance patterns 143.

A relation between the resistance value R and a temperature T of the resistance patterns 143 will be described. The temperature of the resistance patterns 143 is given by the following equation (1):

$$T = C1 \times R + C2, \quad (1)$$

where the coefficient C1 and the coefficient C2 are predetermined constant numbers. Therefore, when the coefficient C1 and the coefficient C2 are known, the temperature T can be obtained from the resistance value R of the resistance patterns 143 in accordance with the equation (1). Hereinafter, the coefficients C1 and C2 will be described.

When a resistance value at a temperature T1 is R1 and a resistance value at a temperature T2 is R2, the following equations (2) and (3) are established from the equation (1):

$$T1 = C1 \times R1 + C2, \quad (2)$$

$$T2 = C1 \times R2 + C2, \quad (3)$$

where a ratio between the resistance values R1 and R2 is $\alpha$. That is, the following equation (4) is established.

$$\alpha = R2/R1. \quad (4)$$

Then, the following equation (5) is obtained from the equations (2), (3) and (4).

$$C2 = (T1 \times \alpha - T2)/(\alpha - 1), \quad (5)$$

where α is a value determined by a material of the resistance patterns 143. That is, the value does not depend on a width of lines or a thickness of the resistance patterns 143 in which non-uniformity occurs in a manufacturing process. Therefore, in the heat generating chips 140 using the same material and having the same structure, a difference of the coefficient C2 between each of the heat generating chips 140 is remarkably small. For obtaining the coefficient C2, it is necessary to measure the resistance value at two different temperatures. However, the difference between each of the heat generating chips 140 is so small that it is not necessary to measure the values of all the heat generating chips 140. Therefore, for example, a sampling inspection is carried out for every manufacturing lot of the heat generating chips 140 to calculate an average value, whereby the coefficient C2 of the heat generating chips 140 of the lot can be obtained with sufficient precision.

When the coefficient C2 is known, the resistance value R of the resistance patterns 143 at a certain temperature T is represented by the following equation (6).

$$C1=(T-C2)/R. \tag{6}$$

As apparent from this equation, when the coefficient C2 is known, the coefficient C1 can be acquired by measuring the resistance value at one certain temperature.

Here, the coefficient C1 depends on the width of the lines or the thickness of the resistance pattern 143, and comparatively large non-uniformity easily occurs in the manufacturing process. Therefore, it is desired that the coefficient C1 is measured for each of the treatment tool.

From the above, in the present embodiment, the coefficient C2 is obtained, for example, by the average value of the sampling inspection of each manufacturing lot or the like in advance. Then, this value of the coefficient C2 is stored in the memory 123 disposed in the energy treatment tool 120 as described above. On the other hand, the coefficient C1 is measured in the initial setting processing during use.

Figure 8:
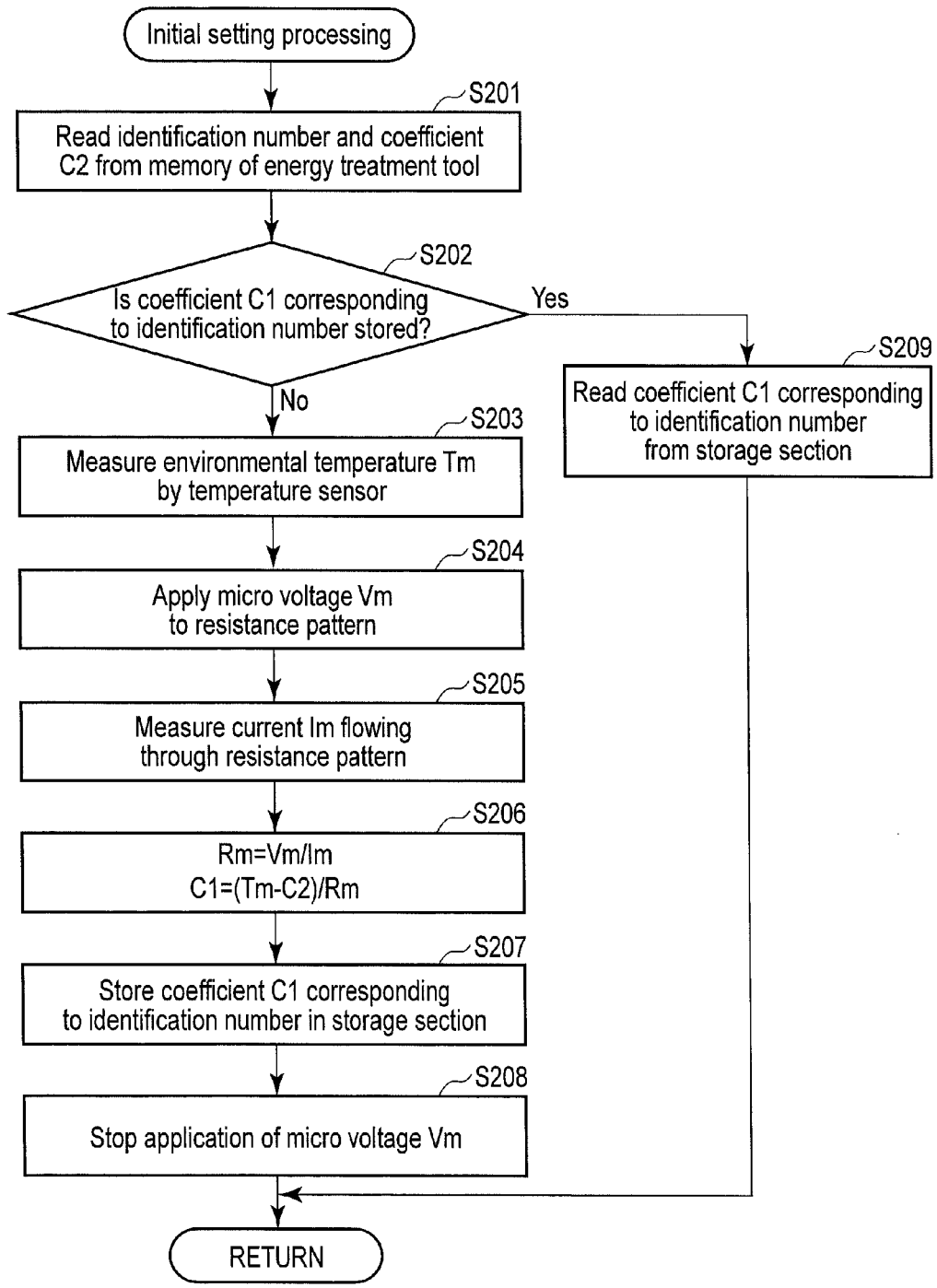
FIG. 8 is a flowchart showing one example of initial setting processing by the control section of the treatment device for the medical treatment according to the one embodiment of the present invention.

An example of the initial setting processing in the present embodiment will be described with reference to a flowchart shown in FIG. 8. In step S201, the control section 180 reads the identification number and the value of the coefficient C2 of the energy treatment tool 120 from the memory 123 of the energy treatment tool 120. In step S202, the control section 180 determines whether or not the coefficient C1 corresponding to the identification number is stored in the storage section 187.

When it is determined in the determination of the step S202 that the coefficient C1 corresponding to the identification number is not stored in the storage section 187, the processing goes to step S203. In the step S203, the control section 180 acquires an environmental temperature Tm measured from the temperature sensor 189 disposed in the controller 170. In the present embodiment, the environmental temperature Tm is acquired as a calibration temperature which is a temperature for use in calculation of the coefficient C1. In step S204, the control section 180 causes the heat generating chip driving circuit 182 to apply a low voltage Vm to the resistance patterns 143 of the heat generating chips 140. In step S205, the control section 180 causes the heat generating chip driving circuit 182 to measure a current Im flowing through the resistance patterns 143, and acquires the measured current Im.

In step S206, the control section 180 calculates a resistance value Rm of the resistance patterns 143 in accordance with the following equation (7).

$$Rm=Vm/Im. \tag{7}$$

Furthermore, the coefficient C1 is calculated in accordance with the following equation (8) on the basis of the obtained Rm, the coefficient C2 acquired in the step S201, the environmental temperature Tm measured in the step S203, and the equation (6).

$$C1=(Tm-C2)/Rm. \tag{8}$$

It is to be noted that this measurement is performed immediately after the connection of the cable 160 to the connector 165, and hence it can be considered that the temperature of the heat generating chip is equal to the environmental temperature.

In step S207, the control section 180 associates the identification number read in the step S201 with the coefficient C1 calculated in the step S206, to store the coefficient in the storage section 187. In step S208, the control section 180 causes the heat generating chip driving circuit 182 to stop the application of the low voltage Vm to the resistance patterns 143. Afterward, the processing returns to the step S102 of the processing shown in FIG. 7 by use of the coefficients C1 and C2 as return values.

On the other hand, when it is determined in the determination of the step S202 that the coefficient C1 corresponding to the identification number is stored in the storage section 187, the control section 180, in step S209, does not perform the calculation of the coefficient C1, but reads the coefficient C1 corresponding to the stored identification number from the storage section 187. Afterward, the processing returns to the step S102 by use of the coefficients C1 and C2 as the return values.

It is to be noted that the processing procedure described herein is one example, and a processing order can suitably be changed. For example, the step S203 can be performed after the step S205, and the step S208 can be performed after the step S205.

Figure 9:
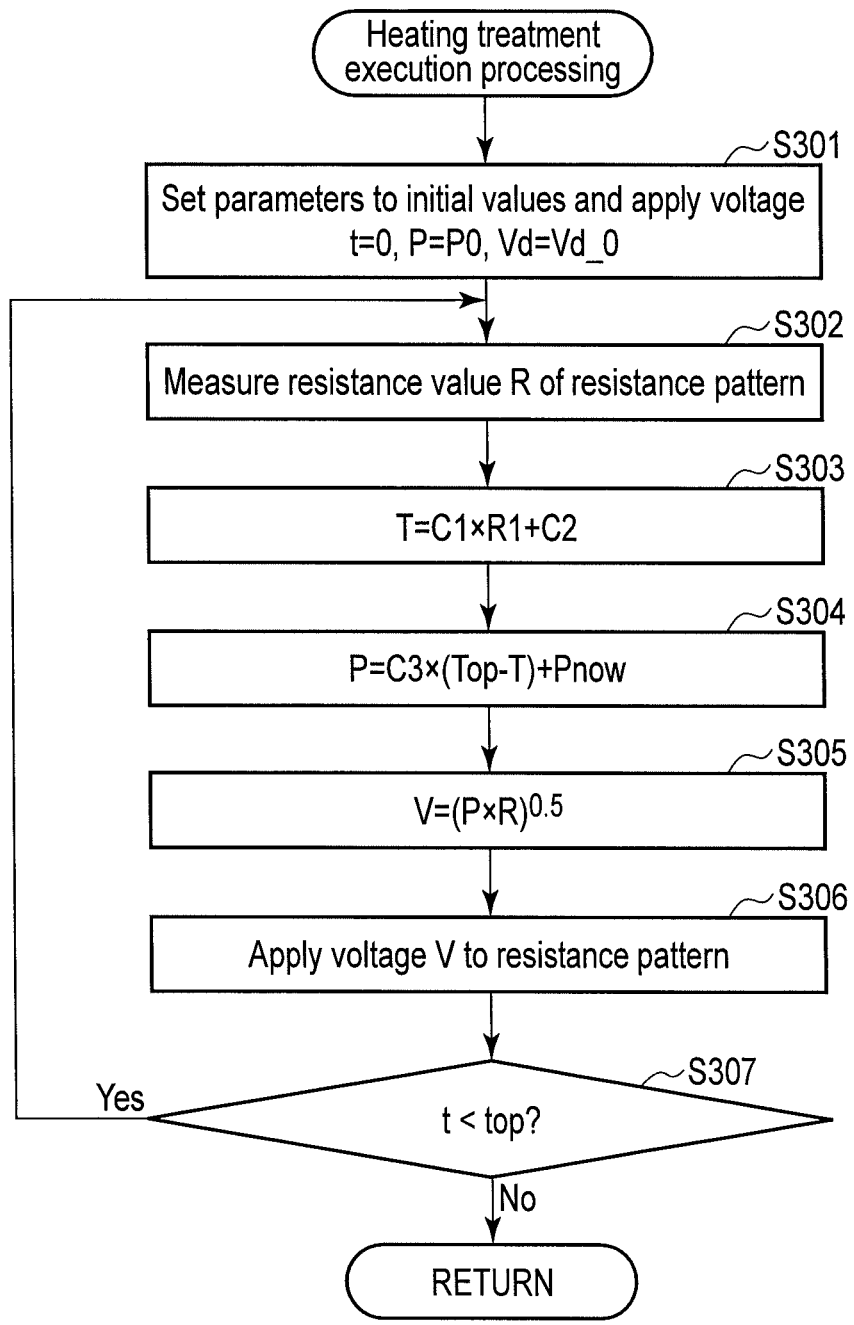
FIG. 9 is a flowchart showing one example of heating treatment execution processing by the control section of the treatment device for the medical treatment according to the one embodiment of the present invention.

In the present embodiment, in the heating treatment execution processing of the step S107, feedback control of the power to be introduced into the heat generating chips 140 is executed by use of the coefficients C1 and C2 obtained as described above. The heating treatment execution processing will be described with reference to a flowchart shown in FIG. 9.

In step S301, the control section 180 sets various parameters to initial values, and causes the heat generating chip driving circuit 182 to start the introduction of the power into the resistance patterns 143. For example, an elapsed time t is set to 0, an introduction power P is set to an initial introduction power P0, and a voltage Vd to be applied to the resistance patterns 143 is set to an initial application voltage Vd_0.

In step S302, the control section 180 calculates the resistance value R of the resistance patterns 143 on the basis of the voltage Vd to be applied to the resistance patterns 143, and the current I at this time which is acquired from the heat generating chip driving circuit 182. In step S303, the control section 180 calculates the temperature T of the resistance patterns 143 in accordance with the equation (1). In step S304, the control section 180 calculates the power P to be introduced into the resistance patterns 143 in accordance with the following equation (9):

$$P=C3\times(T_{op}-T)+P\text{now}, \tag{9}$$

where C3 is a control gain, and a predetermined value is given thereto. $T_{op}$ is a desired temperature, and Pnow is the power which is being introduced now. Here, simple proportional control in which the control gain is C3 is used, but PID control may be used to perform more stable control.

In step S305, the control section 180 calculates an application voltage V in accordance with the following equation (10).

$$V=(P \times R)^{0.5}. \tag{10}$$

In step S306, the control section 180 causes the heat generating chip driving circuit 182 to apply the calculated application voltage V to the resistance patterns 143.

In step S307, the control section 180 determines whether or not the elapsed time t is smaller than the treatment time $t_{op}$. When the elapsed time t is smaller than the treatment time $t_{op}$, the processing returns to the step S302. On the other hand, when the elapsed time t is the treatment time $t_{op}$ or more, the heating treatment execution processing ends, and the processing returns to the step S107 of the processing shown in FIG. 7. While the processing of the step S302 to the step S307 is repeated as above, the power P to be introduced into the resistance patterns 143 is subjected to the feedback control.

According to the present embodiment, for obtaining the coefficient C1 and the coefficient C2, it is not necessary to measure the respective resistance values of all the energy treatment tools 120 as objects at the temperatures. The coefficient C2 is stored in the energy treatment tool 120 in advance, and the resistance value is measured at a single temperature, whereby the coefficient C1 can be obtained with high precision. Therefore, the coefficient C1 and the coefficient C2 can be obtained simply by measuring the resistance value at the environmental temperature prior to the use of each of the energy treatment tools 120. As a result, it is not necessary to perform the measurement of all the energy treatment tools 120 as the objects in an inspection process during the manufacturing, and hence costs of the inspection process can be lowered.

Moreover, in the present embodiment, the measurement of the resistance value Rm during the calculation of the coefficient C1 is performed by the application of the low voltage Vm, and hence the heat generating chips 140 do not reach a high temperature. Furthermore, this measurement is performed immediately after the connection of the cable 160 to the connector 165, and hence it can be considered that the temperature of the heat generating chips is equal to the environmental temperature. As compared with a case where the temperature of the heat generating chips is raised or lowered, the temperature T can stably be acquired, and hence the coefficient C1 is calculated with high precision.

Furthermore, in the calculation of the coefficient C1, the environmental temperature is used as the calibration temperature. Therefore, when the temperature sensor 189 is disposed in the controller 170, a temperature sensor for acquiring the temperature of the resistance patterns 143 does not have to be disposed for each of the energy treatment tools 120. Moreover, when the precision is slightly sacrificed or when the treatment tool is used in a place where the environmental temperature is stable, the temperature sensor 189 is not disposed, but it is presumed that the environmental temperature is constant, for example, at 25° C. or the like, and by use of the temperature as the calibration temperature, similar processing can be performed.

Moreover, according to the present embodiment, the measurement of the coefficient C1 is performed by using the controller 170 which actually drives the energy treatment tool 120, and hence an individual difference of the controller 170, for example, a parasitic resistance of an inner wiring line, an offset of an amplifier, or the like is corrected. Therefore, the temperature control of the heat generating chips 140 can be executed with higher precision.

Furthermore, the value of the coefficient C1 measured once is reused for the same controller 170. Therefore, for example, when the energy treatment tool 120 is disconnected from the controller 170 temporarily for some reason after performing a heating medical treatment and reconnected immediately, the coefficient C1 is not updated to a wrong value, even if there is a large temperature difference between the heat generating chips 140 and the temperature sensor 189 of the controller 170 due to the residual heat of the heat generating chips 140. It is to be noted that in the present embodiment, the calculated value of the coefficient C1 is stored in the storage section 187, but needless to say, a similar effect can be obtained even when the value is stored in the memory 123.

Moreover, in the present embodiment, the coefficient C2 is stored in the memory 123 of the energy treatment tool 120, and hence the energy treatment tool 120 in which the material of the resistance patterns 143 is different can be driven by the same controller 170. It is to be noted that when the resistance patterns 143 are made of a single material and non-uniformity between the manufacturing lots is very small, the coefficient C2 may be stored, for example, in the storage section 187 of the energy treatment tool 120. Furthermore, a relation between the identification number of the energy treatment tool 120 and the coefficient C2 corresponding to the identification number may be acquired, for example, on line by the controller 170, or the information may be acquired via media.

Furthermore, in the present embodiment, a relation between the identification number and the calculated coefficient C1 corresponding to the identification number is stored in the storage section 187 of the controller 170, but the relation may be stored in the memory 123 disposed in the energy treatment tool 120 or another memory.

Additionally, in the present embodiment, the temperature sensor 189 for measuring the environmental temperature is disposed in the controller 170, but a temperature sensor may be disposed in the energy treatment tool 120 and a measured value of the temperature sensor may be read by the controller 170. In this case, the temperature sensor is especially suitably disposed in the vicinity of the heat generating chips 140. In this case, the calibration temperature for use in calculating the coefficient C1 is not limited to the environmental temperature.

Moreover, in the present embodiment, when the temperature of the resistance patterns 143 is calculated from the resistance value thereof, the equation (1) is used, but when the dependency of a resistance temperature coefficient on a temperature is taken into consideration to perform temperature measurement with higher precision, the following equation (11) can be used.

$$T=C1' \times R^2+C1 \times R+C2. \tag{11}$$

In this case, the dependency of the resistance temperature coefficient on the temperature is concerned with a coefficient C1'. Here, C1' also depends on the material of the resistance patterns 143 similarly to C1. Therefore, when the coefficient C1' is used, this coefficient may be stored in the memory 123 similarly to C1.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment device for a medical treatment which heats a biotissue at a desired temperature to perform the medical treatment, the device comprising:
a treatment tool which includes:
a heat transfer portion which is configured to come in contact with the biotissue to transfer heat to the biotissue, and
a resistance element into which power is configured to be supplied to heat the heat transfer portion;
a controller which is detachably attached to the treatment tool, and configured to measure a resistance value R of the resistance element and to supply the power to the resistance element so as to control a temperature of the heat transfer portion to heat the biotissue at the desired temperature; and
a storage section which is disposed in the treatment tool or the controller to store a coefficient C2,
wherein the controller is configured to:
calculate a coefficient C1 before the medical treatment while the treatment tool and the controller are connected to each other, based on a calibration temperature Tc, the stored coefficient C2 and a measured resistance value Rc of the resistance element, in accordance with $C1=(Tc-C2)/Rc,$ calculate a temperature T of the resistance element, using the coefficient C1, the resistance value R and the coefficient C2, in accordance with $T=C1 \times R+C2,$ and control the temperature of the heat transfer portion by use of the temperature T.

2. The treatment device according to claim 1, wherein the controller is further configured to calculate the coefficient C1 after the treatment tool is connected to the controller and prior to start of the heating.

3. The treatment device according to claim 1, wherein the controller is configured to calculate the coefficient C1 using an environmental temperature as the calibration temperature Tc.

4. The treatment device according to claim 3, further comprising:
a temperature sensor disposed in the treatment tool or the controller to measure the environmental temperature.

5. The treatment device according to claim 1, further comprising:
a calculated coefficient storage section disposed in the treatment tool or the controller,
wherein the controller is configured to store the calculated coefficient C1 in the calculated coefficient storage section.

6. The treatment device according to claim 5, wherein the controller is configured to calculate the coefficient C1 when the treatment tool is connected to the controller for a first time, and read the coefficient C1 stored in the calculated coefficient storage section when the treatment tool is connected for a second or subsequent time, to control the temperature of the heat transfer portion.

* * * * *